United States Patent
Garakani

(10) Patent No.: US 7,169,162 B2
(45) Date of Patent: Jan. 30, 2007

(54) BALLOON CATHETER

(75) Inventor: Morteza Hemmati Garakani, Margate, FL (US)

(73) Assignee: OrbusNeich Medical, Inc., Fort Lauderdale, FL (US)

( * ) Notice: Subject to any disclaimer, the term of this patent is extended or adjusted under 35 U.S.C. 154(b) by 719 days.

(21) Appl. No.: 10/190,057

(22) Filed: Jul. 3, 2002

(65) Prior Publication Data

US 2004/0006360 A1   Jan. 8, 2004

(51) Int. Cl.
*A61M 29/00* (2006.01)

(52) U.S. Cl. .................................. 606/192

(58) Field of Classification Search ........ 606/191–194; 604/103.04, 103, 103.01, 103.06, 103.08
See application file for complete search history.

(56) References Cited

U.S. PATENT DOCUMENTS

| | | | | |
|---|---|---|---|---|
| 5,300,025 A | * | 4/1994 | Wantink | 604/103.09 |
| 5,387,193 A | * | 2/1995 | Miraki | 604/102.02 |
| 5,490,837 A | | 2/1996 | Blaeser et al. | |
| 5,634,902 A | | 6/1997 | Johnson et al. | |
| 6,575,958 B1 | * | 6/2003 | Happ et al. | 604/525 |
| 2001/0011180 A1 | | 8/2001 | Fitzmaurice et al. | |

FOREIGN PATENT DOCUMENTS

| | | |
|---|---|---|
| DE | 44 15 107 A1 | 3/1994 |
| EP | 1 084 728 A1 | 3/2001 |
| WO | WO 95/09668 | 4/1995 |

* cited by examiner

*Primary Examiner*—(Jackie) Tan-Uyen T. Ho
(74) *Attorney, Agent, or Firm*—White & Case LLP

(57) ABSTRACT

A balloon catheter comprises a shaft including a tubular having a relatively rigid proximal shaft section and a distal shaft section, each section connected to one another through a flexible transition member, and an inflatable balloon extending at a distal portion of the distal shaft section. The proximal and distal shaft sections define an inflation lumen extending therein which is in fluid communication with an interior of the balloon to allow inflation pressure to the balloon. The distal shaft further comprises a guide wire lumen to receive a guide wire. The guide wire lumen has a guide wire inlet, located between the end portion of the proximal shaft section and the balloon, and a guide wire outlet, located distally to the balloon and leading to an exterior of the catheter. The balloon catheter can be used for coronary angioplasty.

11 Claims, 2 Drawing Sheets

BALLOON CATHETER

The present invention relates to a balloon catheter comprising a shaft including a mainly tubular relatively rigid proximal shaft section and a distal shaft section, more flexible than the proximal shaft section, attached to a distal end portion of the proximal shaft section, and an inflatable balloon extending at a distal portion of the distal shaft section, the proximal and distal shaft section defining an inflation lumen extending therein which is in fluid communication with an interior of the balloon to allow inflation pressure to the balloon, the distal shaft section comprising a guide wire lumen to receive a guide wire, which guide wire lumen has a guide wire inlet, located between the end portion of the proximal shaft section and the balloon, and a guide wire outlet, located distally to the balloon and leading to an exterior of the catheter, in which a flexible transition member is attached to the distal end portion of the proximal shaft segment extending into the distal shaft segment. In particular the present invention relates to a dilatation balloon catheter of the so called "rapid exchange over-the-wire" type having a relatively short distal guide wire lumen extending through part of the distal shaft section, including the balloon area. Such a balloon catheter is widely used in the field of coronary angioplasty, particularly for percutaneous transluminal coronary angioplasty (PTCA).

Angioplasty procedures have gained wide acceptance as efficient and effective methods of treating various types of vascular disease. In particular, angioplasty is widely used for opening stenosis in the coronary arteries, although it may be used for the treatment of stenosis in other areas of the body as well. The most widely used form of angioplasty requires a dilatation catheter carrying an inflatable balloon at its distal end. Typically, a hollow guide catheter is initially placed, percutaneously, in the femoral artery of the patient and is advanced along the descending aorta over the aortic arch and into the ascending aorta that leads from the heart. The distal end of the guide catheter is specially shaped so that the distal tip of the guide catheter will easily lodge in the entrance to the right or left coronary artery. This guide catheter is used in rapidly guiding the dilatation catheter through the vascular system to a position slightly beyond said entrance. Using, fluoroscopy, the physician guides the dilatation catheter the remaining distance across a strongly curved part of the trajectory through the vascular system until the balloon is positioned to cross the stenosis. The balloon is then inflated by supplying fluid under pressure through the inflation lumen extending from a proximal end of the catheter to within the balloon. The inflation of the balloon causes stretching of the artery and pressing of the lesion into the artery wall, thus reestablishing an acceptable blood flow through the artery.

In order to be readily advanced to the place of treatment, the catheter should preferably fulfill a number of mutually opposite requirements. First of all the catheter should be pushable such that pushing forces exerted on its proximal end are really transmitted to the distal tip. Also torque forces need to be transmitted as undisturbed as possible throughout the catheter to enhance the steerability and responsiveness of the device. The transmission of these forces is served by a rigid and stiff catheter shaft. However, the catheter should also be sufficiently flexible to be able to follow the natural anatomy of the vasculature, especially the strongly curved trajectory in the coronary region, and to reach the stenosis. The latter is generally referred to as the trackability of the catheter. In order to comply with both these requirements, the balloon catheter of the kind described in the opening paragraph comprises a composite shaft design with a distal section which is sufficiently flexible to comply with the natural anatomy of the coronary arteries, offering the required trackabilty, and with a proximal shaft section, which is more rigid to provide the required pushability and steerability.

A ballon catheter with such a composite catheter is for instance known from European patent application 580.845. This catheter comprises a proximal shaft section defined by a tube formed from hypodermic metal, followed by a distal shaft section of plastic tubing substantially more flexible than the proximal shaft section. The relatively stiff metal tube is capable of transmitting pushing and steering forces with little or no loss from its proximal end to its distal end, already at a small profile, to provide the desired pushability and steerability of the catheter, but would be too rigid to follow the strongly curved coronary arteries. In practice, however, the proximal shaft section only reaches to the entrance to the right or left coronary artery in a substantially linear trajectory. The flexible plastic tubing forming the distal shaft section, on the other hand, extends beyond said entrance but is sufficiently bendable to follow the curves of the coronary vessels.

Although a composite shaft design as described above is capable of achieving both the required pushability and steerability on the one hand and the desired trackability on the other, the relatively large difference in stiffness between the proximal and distal shaft section makes the catheter relatively prone to kinking and buckling at the transition between both shaft segments, notably at the area which is left unsupported by a guide wire inserted in the guide wire lumen. This will not only reduce the responsiveness and pushability of the catheter but could even lead to significant closure of the inflation lumen from the proximal shaft section to within the distal shaft section. It will be clear that a closed inflation lumen renders the catheter useless.

To alleviate these problems associated with the transition between the relatively stiff, metallic proximal shaft section and the considerably more flexible distal shaft section the known catheter comprises a transition member in the form of a core wire to bridge the gap between the proximal shaft section and the guide wire lumen. This core wire gives support to the otherwise unsupported portion of the distal shaft section. The remaining part of the distal shaft section will be supported by the guide wire once it is received in the guide wire lumen, so that the catheter will have support substantially along its entire length. This significantly reduces its tendency to bend or buckle at a specific area. However, in order to connect the core wire to the proximal shaft section, it is inserted slightly into the distal end of the metallic tube and brazed to the interior wall of it. As such it extends within the inflation lumen running through the metallic tube, providing a significant obstruction of inflation fluid. Moreover, the proximal part of the core wire extending within the metallic tube is hardly accessible for brazing, which easily gives rise to a poor bond and hence to a reduced reliability of the connection.

The present invention has inter alia for its object to provide for a balloon catheter of the kind referred to in the opening paragraph with a reduced tendency to bend, kink or buckle inside a guiding catheter, while being advanced in the patient's body, void of the aforementioned problems associated with the known catheter.

To this end a balloon catheter of the type described in the opening paragraph is, according to the invention, characterized in that the distal end portion of the proximal shaft section is skived and in that the transition member is secured to the proximal shaft section substantially all along the skived part of distal end portion of the proximal shaft section. The skived end portion of the proximal shaft section offers plenty readily accessible connection area to facilitate a reliable bond between the transition member and the proximal shaft section. Because the inflation fluid is entirely free to flow around and pass the transition member at this area, no noticeable obstruction of the inflation pressure will be experienced while expanding the balloon at the distal tip of the catheter. The transition member supports the catheter shaft over the otherwise unsupported area between the proximal shaft section and the guide wire lumen, thus counteracting considerable kinking and buckling of the catheter. As such the catheter according to the invention provides for a sleek profile dilatation catheter with unsurpassed mechanical and dynamical characteristics.

In a special embodiment, the catheter according to the invention is characterized in that a proximal end portion of the transition member extends inside a tubular portion of the proximal shaft section and in that said proximal end portion of said transition member touches an inside wall of said tubular portion of said proximal shaft section while having a smaller cross section than a portion of said transition member disposed more distally. The transition member thus provides continuous, integral support of the weakened, skived portion of the proximal shaft section in order to avoid kinking of the catheter at this area. The specific cross-sectional profile of the proximal end of the transition member reduces the obstruction which would otherwise be created by the transition member inside the tubular part of the proximal shaft section. As a result, inflation fluid is nonetheless capable of flowing freely past the transition member. In a yet more specific embodiment, the catheter according to the invention is characterized in that said transition member comprises a core wire and in that the proximal end of said core wire is provided with a notch at a side across from the inside wall of the tubular portion of the proximal shaft segment. This notch reduces the flow resistance of the inflation fluid, while maintaining the contact area between the core wire and the proximal shaft section.

In order to a facilitate a gradual increase in flexibility of the distal shaft section a preferred embodiment of the catheter according to the invention is characterized in that at least a distal part of said transition member has a diameter generally diminishing in a distal direction. The generally diminishing diameter will generally lead to a gradually diminishing stiffness of this portion of the catheter shaft. As such it avoids abrupt changes in stiffness which could otherwise again induce some sensitivity to buckling and kinking. Preferably the distal end of the transition member is disposed more distally than the entrance to the guide wire lumen so that the guide wire will be capable of taking over the support of the catheter shaft where the transition member has lost too much of its a rigidity to serve this purpose.

Although the transition member and the proximal shaft section may be connected in different manners, very good results have been obtained in a special embodiment of the catheter, which according to the invention is characterized in that the transition member and the distal portion of the proximal shaft section are glued together.

Hereinafter, the invention will be described in more detail with reference to an illustrative embodiment and an accompanying drawing. In the drawing.

Figure 1:
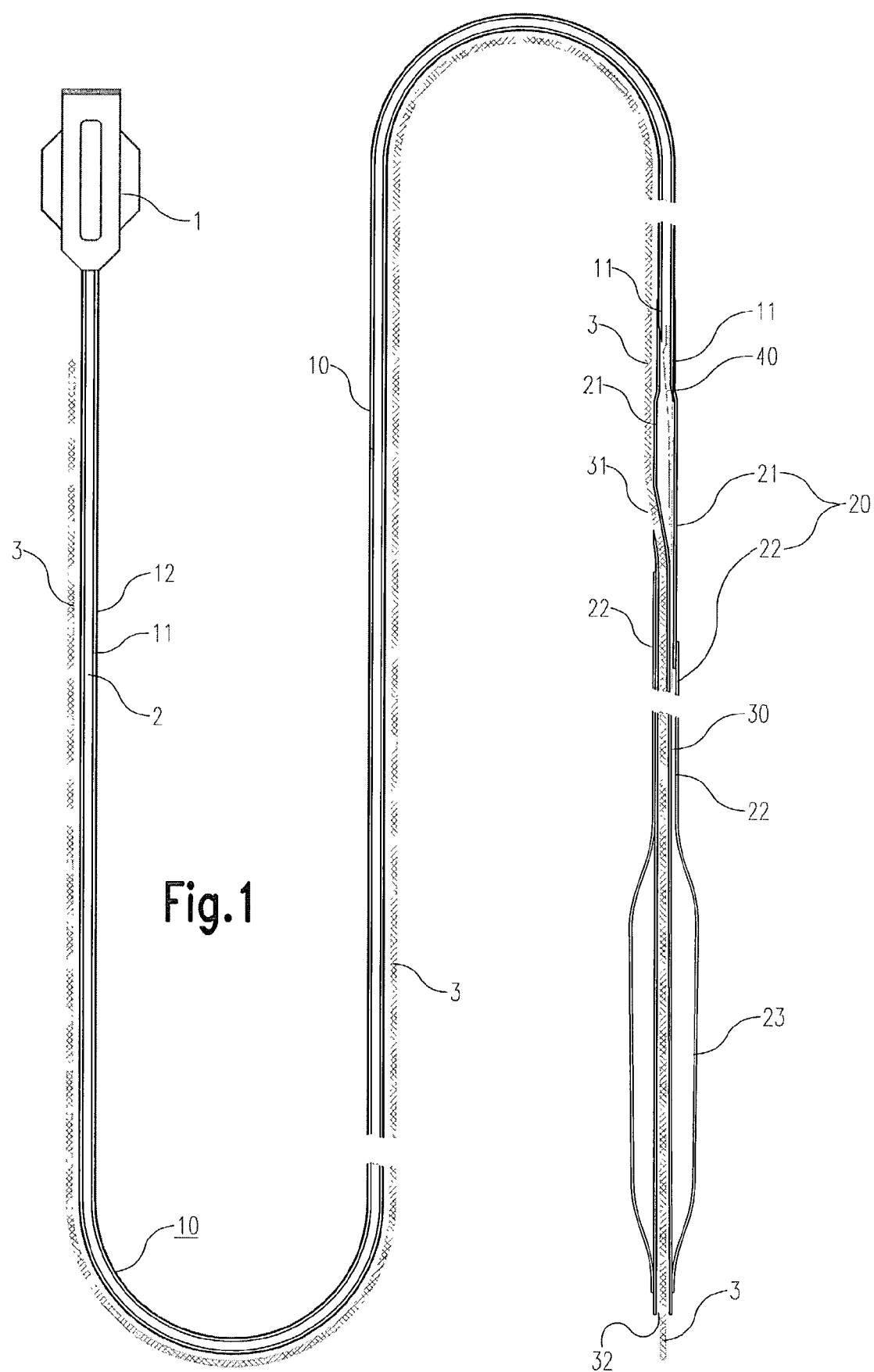
FIG. 1 shows a longitudinal cross section of an embodiment of a balloon dilatation catheter according to the invention.

It should be noticed that the drawings are not drawn exactly to scale. In particular some dimensions may have been exaggerated to more or less extend for sake of clarity.

Corresponding or similar parts in the drawings are generally denoted by the same reference sign.

The catheter of FIG. 1 comprises a proximal shaft section 10 which carries at its utmost proximal end a so-called Luer fitting 1 for connecting the catheter in a conventional manner to inflation equipment. Said equipment enables the delivery of a suitable inflation fluid under pressure which is guided through an inflation lumen 2 extending within the catheter to the interior of an inflatable balloon 23 provided at the distal end of the catheter.

In practice, the catheter is advanced through a guide catheter, not shown, inside the patient's vasculature to the entrance of one of the coronary arteries. The proximal shaft section 10 of the catheter extends approximately all along the length of the guide catheter. In order to improve the pushability and steerability the catheter should preferably be relatively rigid and stiff to enable forces exerted on its proximal end to be transmitted with little or no loss to the distal end. To this end a metallic tubular member 11 is, according to the invention, used for the proximal shaft section of the catheter. In the present embodiment said member 11 is made of hypodermic metal, a so-called hypotube, coated with a lubricious coating 12 to reduce the amount of friction between the inside wall of the guide catheter and the dilatation catheter. This coating consists of a thin layer of Teflon® or other lubricious plastic or polymer, but other materials are also feasible within the scope of the present invention. Such a hypotube assembly greatly reduces the catheter's tendency to bend or buckle inside the guide catheter while it is being pushed forward. However, the bending nature of the smaller coronary arteries requires much more flexibility to allow the catheter following to follow tile natural anatomy of these vessels.

Figure 2:
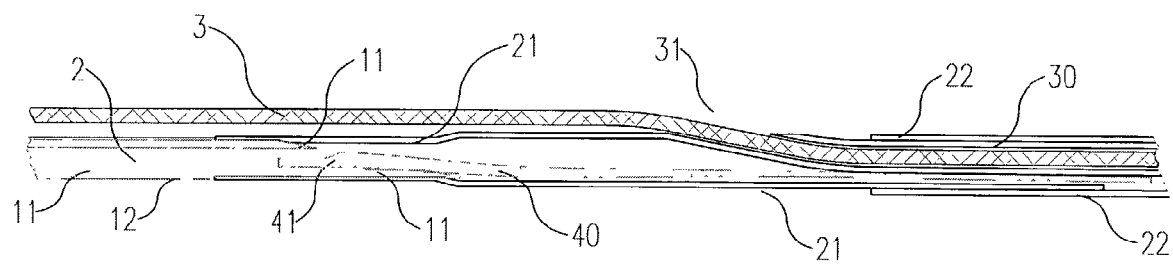
FIG. 2 shows a detailed representation of part of the catheter of FIG. 1.

The catheter hence comprises a distal shaft section 20 which is much more flexible to provide for this so-called trackability. In this embodiment, the distal shaft section comprises an intermediate sleeve segment 21 and a balloon segment 22. Both parts 21, 22 of the distal shaft section 20 are made of a piece of plastic tubing of low density polyethylene, polyvinylchloride, Nylon® or any other suitable plastic, which is sufficiently flexible to follow any bends in the coronary arteries. The intermediate sleeve segment directly connects to the proximal shaft section 10 and comprises a proximal entry port 31 to a guidewire lumen 30 extending inside the distal shaft section 20 of the catheter, alongside or, as in this case, coaxial to the inflation lumen. This part of the catheter is shown in greater detail in FIG. 2 of the drawings.

The guidewire lumen 30, during use, accommodates a guide wire 3 extending for the majority alongside the proximal shaft section 10 of the catheter and, for the rest, inside said guidewire lumen 30. The guidewire 3 enters the guidewire lumen 30 through the guidewire lumen inlet 31 at the intermediate sleeve section 21, which is thus located between the distal end of the proximal shaft section 11 and the balloon segment 22, to exit the catheter through a guide wire lumen outlet 32 at the distal tip of the catheter. The guidewire 3 is used for rapid exchanging of the catheter for another one, when necessary. With the guidewire 3 remaining in place, the catheter may be pulled back to be replaced by another one which may be advanced relatively rapidly to the treatment spot by simply sliding it over the guidewire. The guidewire 3 thereby guides the catheter directly to the right location. Because of this feature, a catheter of the present kind is often referred to as a rapid exchange over-the-wire catheter.

The balloon section carries an inflatable balloon 23. The interior of the balloon 23 is in fluid communication with the inflation lumen 2 which extends all the way down from the Luer fitting 1 through the proximal shaft section and the intermediate sleeve segment 21 to within the balloon segment 22 of the distal section 20 of the catheter. The balloon is fabricated from a suitable pre-shaped plastic sleeve capable of withstanding a large internal pressure. On application of inflation pressure the balloon will expand to a predefined expanded diameter to widen the vessel correspondingly. A metallic stent member, not shown, may have been provided over the balloon and is expanded along with the balloon to be left behind in the vessel for providing continuous support of the vessel wall after the treatment has been completed.

In order to avoid kinking of the catheter at the transition from the relatively rigid proximal shaft section 10 to the more flexible distal shaft section 20, a transition member 40 is provided to support the otherwise unsupported area of the catheter between the hypotube 11 and the guidewire lumen inlet 31. With a guidewire 3 inserted in the guidewire lumen 30, said transition member 40 bridges the gap inside the catheter shaft between the metallic hypotube 11 and the metallic guidewire 3. In the present embodiment the transition member 40 comprises a metallic core wire having a flexibility generally in between that of the proximal shaft section 10 and the distal shaft section 20. The core wire 40 is firmly connected to the hypotube 11 by brazing, gluing or any other suitable means. With a length of about 286 millimeter, the core wire 40 extends well beyond the guidewire lumen inlet 31.

In accordance with the present invention, the hypotube 11 is skived at its distal end in order to provide sufficient contact area for a reliable bond between the core wire 40 and the hypotube 11. The skived portion of the hypotube extends over a predetermined length of roughly between 60 and 70 millimeters to accommodate a proximal end of the core wire 40. The skived end portion of the hypotube not only provides the necessary contact area but moreover exposes said contact area in order to render it readily accessible for the connection technique to be used. In this embodiment the core wire 40 is glued to the hypotube 11 by means of a UV curing adhesive. Due to the skived portion, the entire contact area may be exposed to UV curing radiation. Moreover, because the inflation fluid is no longer confined to the interior of the hypotube 11 at this skived area it may flow freely past the core wire 40. As a result, the core wire 40 presents no substantial obstruction to the inflation fluid while the balloon 23 is being inflated.

Figure 3:
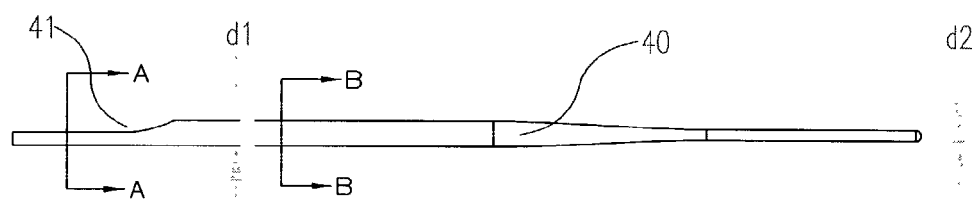
FIG. 3 shows a detailed cross section of a transition element applied in the catheter of FIG. 1.
Figure 4:
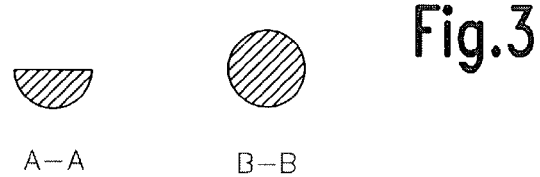
FIG. 4 is a perspective view of the transition element of FIG. 3.
Figure 4:
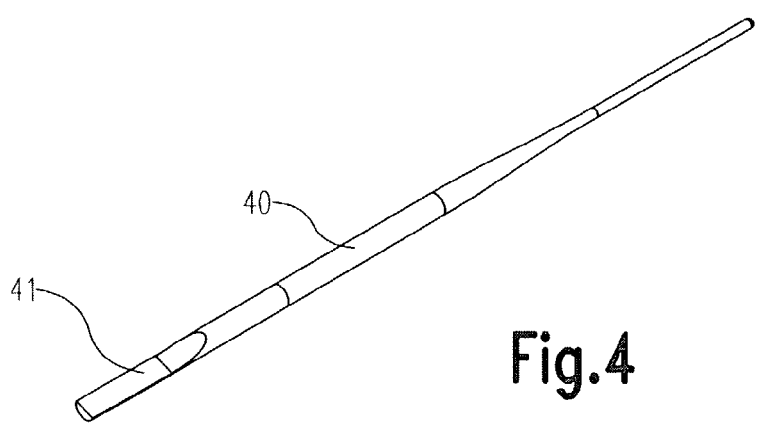

Due to the skived structure, the hypotube 11 loses a considerable amount of its rigidity at its distal area. In order to avoid any kinking of the skived distal portion of the hypotube, the core wire 40 preferably extends a little inside the tubular. i.e non-skived, part of the hypotube to give overall support. In this embodiment, the proximal end of the core wire 40 lies about 3–5 millimeter inside the tubular part of the proximal shaft section 10. In order to avoid a substantial obstruction of the inflation fluid, which could otherwise be caused in this manner, the proximal end of the core wire 40 is provided with a notch 41, see particularly FIGS. 3 and 4. This notch 41 is about 5–7 millimeter long and clears up to about 50% of the cross sectional area of the core wire, which appears sufficient to allow the inflation fluid to flow undisturbed from the Luer fitting 1 to the balloon 23 and vice versa. The notch 41 is provided at a side across from the contact area between the core wire 40 and the interior wall of the proximal shaft section 10 in order to maintain sufficient area for a reliable bond. In stead of a notch 41 also another bulk reducing operation may be followed to provide the proximal portion of the transition member 40, intended to extend a little inside the tubular portion of the proximal shaft section 10, with a smaller cross section than a portion disposed more distally. From a hydrodynamical point of view said proximal portion is preferably given a gradual profile, like that of a notch or skive, in order to avoid substantial turbulence of the inflation fluid while the balloon 23 is being inflated or deflated.

Preferably the transition member 40 should offer a smooth transition in flexibility from the metallic proximal shaft section to the plastic distal shaft section. To this end the core wire 40 gradually tapers down in the distal, direction. In this example the core wire has a proximal diameter d1, see FIG. 3, of about 0.31 millimeter, tapering down to a distal diameter d2 of about 0.13 millimeter at its distal tip over a length of about 279 millimeters. Because of this gradually diminishing cross section, the flexibility of the core wire 40 gradually rises, so that a very smooth transition to the plastic distal tubing is obtained.

As a result the catheter of the present embodiment may be advanced through the patient's vasculature with a very good pushability and steerability, while maintaining a high trackability, without any substantial susceptibility to buckling or kinking.

Although the present invention has been described in greater detail along the lines of merely a single embodiment, it will be appreciated that the present invention is by no means limited to this embodiment. On the contrary many modifications and other embodiments are feasible to a skilled practitioner without departing from the scope and spirit of the present invention. As such, the materials and dimensions used in the foregoing embodiment may be replaced by other existing or newly developed materials and other dimensions to offer the best practical performance. Also other types of transition elements may be used, although very good results are achieved with the core wire of the example.

The invention claimed is:

1. A balloon catheter comprising a shaft including a mainly tubular relatively rigid proximal shaft section and a distal shaft section, more flexible than the proximal shaft section, attached to a distal end portion of the proximal shaft section and an inflatable balloon extending at a distal portion of the distal shaft section, the proximal and distal shaft sect ton defining an inflation lumen extending therein, which is in fluid communication with an interior of the balloon to allow inflation pressure to the balloon, the distal shaft section comprising a guide wire lumen to receive a guide wire, which guide wire lumen has a guide wire inlet, located between the end portion of the proximal shaft section and the balloon, and a guide wire outlet, located distally to the balloon and leading to an exterior of the catheter, in which a flexible transition member is attached to the distal end portion of, the proximal shaft section extending into the distal shaft section, wherein the distal end portion of the proximal shaft section is skived and the transition member is secured to the proximal shaft section substantially all along the skived distal end portion of the proximal shaft section and further wherein a proximal end portion of the transition member extends inside a tubular portion of the proximal shaft section and the proximal end portion of the transition member touches an inside wall of the tubular portion of the proximal shaft section while having a smaller cross section than a portion of the transition member disposed more distally.

2. The balloon catheter according to claim 1, wherein the skived end portion of the proximal shaft section has a predetermined length.

3. The balloon catheter according to claim 1, wherein the transition member comprises a core wire and the proximal end of the core wire is provided with a notch at a side across from the inside wall of the tubular portion of the proximal shaft segment.

4. The balloon catheter according to any one of claims 1, 2 and 3, wherein at least a distal part of the transition member has a diameter generally diminishing in a distal direction.

5. The balloon catheter according to claim 4, wherein the distal part of the transition member has a predetermined length.

6. The balloon catheter according to any one of claims 1, 2 and 3, wherein the transition member and the distal portion of the proximal shaft section are glued together.

7. The balloon catheter according to any one of claims 1, 2 and 3, wherein the transition member has a length between 20 and 30 centimeters.

8. The balloon catheter according to any one of claims 1, 2 and 3, wherein the transition member has a maximum diameter of between 0.25 and 0.35 millimeter.

9. The balloon catheter according to claim 4, wherein the transition member and the distal portion of the proximal shaft section are glued together.

10. The balloon catheter according to claim 4, wherein the transition member has a length between 20 and 30 centimeters.

11. The balloon catheter according to claim 4, wherein the transition member has a maximum diameter of between 0.25 and 0.35 millimeter.

* * * * *